(12) United States Patent
Turkdogan

(10) Patent No.: US 6,328,867 B1
(45) Date of Patent: Dec. 11, 2001

(54) SENSORS FOR MEASURING THE SOLUTE CONTENTS OF LIQUID FERROUS AND NON-FERROUS METALS

(76) Inventor: Ethem Tugrul Turkdogan, 5820 Northumberland St., Pittsburgh, PA (US) 15217

( * ) Notice: Subject to any disclaimer, the term of this patent is extended or adjusted under 35 U.S.C. 154(b) by 0 days.

(21) Appl. No.: 09/564,996

(22) Filed: May 4, 2000

(51) Int. Cl.[7] ........................ G01N 27/416; G01N 27/42; G01N 27/26
(52) U.S. Cl. .................. 204/422; 204/423; 324/425; 324/426; 324/432
(58) Field of Search .................... 324/437, 425, 324/426, 432; 204/422, 423, 408, 421–424, 425, 426, 427, 428, 429; 205/783.5

(56) References Cited

U.S. PATENT DOCUMENTS

| | | | |
|---|---|---|---|
| 3,619,381 | * 11/1971 | Fitterer | 205/783.5 |
| 3,630,874 | * 12/1971 | Olette et al. | 204/422 |
| 3,668,099 | * 6/1972 | Rittiger et al. | 204/423 |
| 3,784,459 | * 1/1974 | Jackson | 204/408 |
| 4,105,507 | * 8/1978 | VonKrusenstierna et al. | 205/783.5 |
| 4,230,603 | * 10/1980 | Olsson et al. | 502/324 |
| 4,342,633 | * 8/1982 | Cure | 204/422 |
| 4,472,196 | * 9/1984 | Argyropoulos et al. | 75/316 |
| 6,177,046 | * 1/2001 | Simkovich et al. | 420/444 |

OTHER PUBLICATIONS

*Steel Research 59*, Iwase, M. et al., No. 10, pp. 433–437 (1988).
*Ironmaking Conference Proceedings*, McDowell, William W. et al., vol. 49, 691–694, (1990).
*Iron and Steelmaking*, Gomyo, K. et al., 20 (3), pp. 87–96 (Mar. 1993).
*Iron and Steelmaking*, Gomyo, K. et al., 18 (7), pp. 71–78 (Jul. 1991).
*Fundamentals of Steelmaking*, Turkdogan, E.T., pp. 91–137 (1996).
*Proc. Roayl Soc.*, McQuillan, A.D., Ser. A204, pp. 309–323, (May 1950).

* cited by examiner

Primary Examiner—Glenn W. Brown
Assistant Examiner—Wasseem H. Hamdan
(74) Attorney, Agent, or Firm—Webb Ziesenheim Logsdon Orkin & Hanson, P.C.

(57) ABSTRACT

An electrochemical field probe for measuring solute concentrations of elements dissolved in a liquid, such as a molten metal bath, generally including a base having a first end, a second end, an external surface, and extending about a longitudinal axis, a reference electrode positioned between the first and second ends of the base, and a glassy electrolyte positioned adjacent the reference electrode, wherein the reference electrode is a Mo substrate coated with a electrode reference material selected from a group including NiAl, graphite, Cr, a compound of Mo and $Mo_3Si$, a compound of Cr and $Cr_2O_3$, a compound of Ti and TiN, a compound of Ti and TiS, and a compound of Th and ThP and the glassy electrolyte is selected from a group including a compound of 38% CaO, 42% $SiO_2$, and 20% $Al_2O_3$, soda glass, pyrex powder, and a pre-fused mixture of cryolite ($Na_3AlF_6$) admixed with approximately 5% to 10% $CaF_2$ (fluorspar) and approximately 4% to 7% $Al_2O_3$.

18 Claims, 1 Drawing Sheet

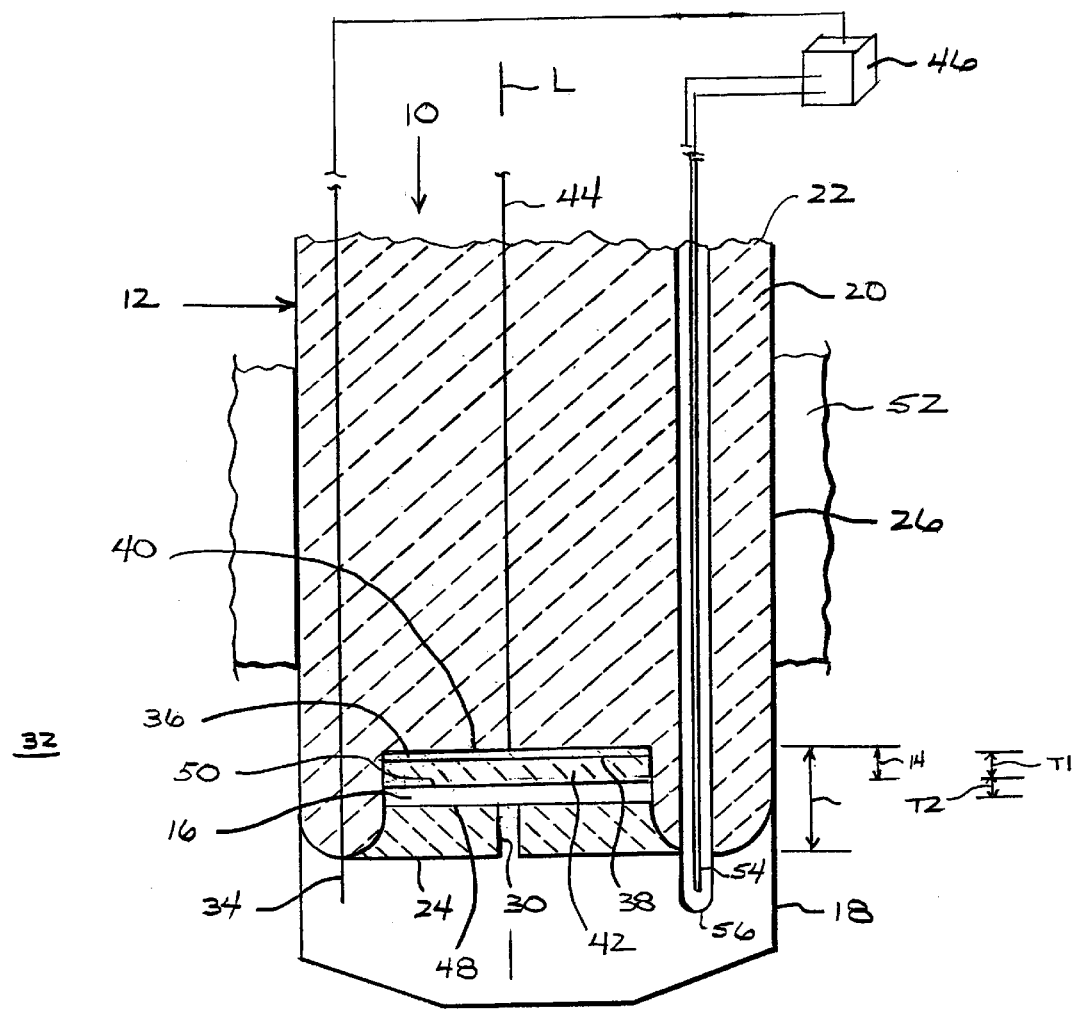
FIG. 1
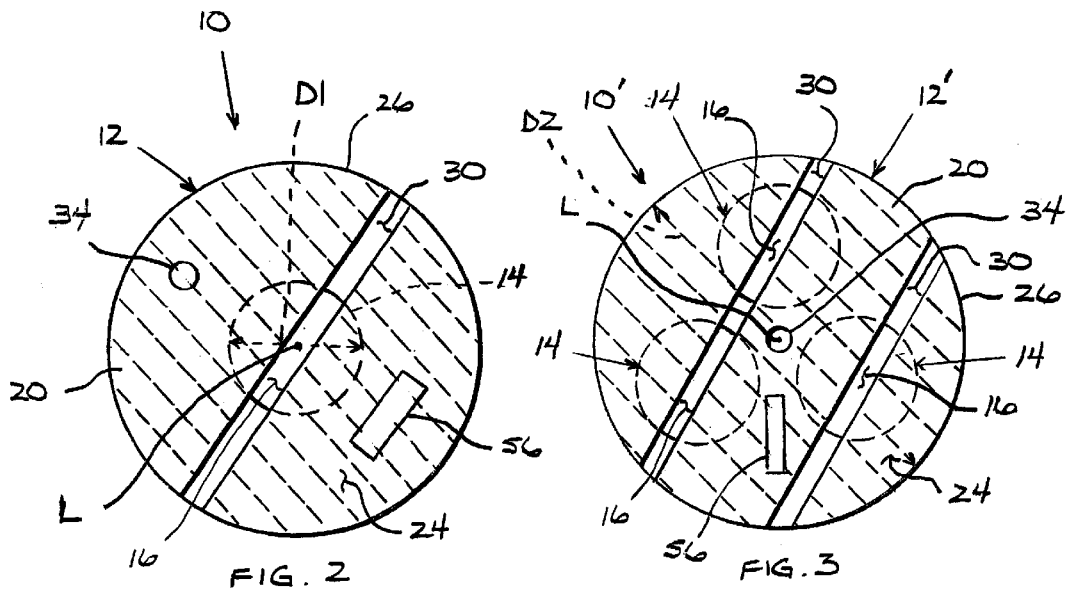
FIG. 2
FIG. 3

SENSORS FOR MEASURING THE SOLUTE CONTENTS OF LIQUID FERROUS AND NON-FERROUS METALS

BACKGROUND OF THE INVENTION

1. Field of the Invention

The present invention relates to electrochemical cell probes and, more particularly, to probes that measure the solute contents of a variety of elements dissolved in liquid metals.

2. Brief Description of the Prior Art

Electrochemical cell (emf) probes are commonly used for in situ measurements of oxygen (O) levels in liquids, such as molten metals. An example includes the CELOX brand oxygen emf probe, available commercially from the Heraeus/Electro-Nite Co. Emf recordings, such as those recorded with the CELOX brand oxygen emf probe, are also used to determine the dissolved aluminum content in deoxidized steel, with the percent of dissolved aluminum in the steel bath being derived from the CELOX brand emf readings for oxygen activity and aluminum thermodynamic data compiled by Hultgren et al. (see "Selected Values of Thermodynamic Properties of Metals and Alloys", John Wiley, New York, 1974), on the assumption that the deoxidation product is pure $Al_2O_3$. However, no detailed study has been made to evaluate the uncertainty limits of the calculated aluminum content.

Many of the commercial oxygen emf probes have three main deficiencies. First, the oxygen emf probes have a thin wall $ZrO_2(MgO)$ electrolyte (~1 mm) and at very low oxygen contents, such as with aluminum deoxidation of steel, there is some electronic conduction in the $ZrO_2(MgO)$ electrolyte. Consequently, the oxygen emf probe registers an emf reading that is somewhat higher than with an electrolyte where the electronic conduction is negligibly small. A second deficiency is that at high oxygen contents, there is rapid oxygen diffusion from the melt through the thin wall electrolyte, causing polarization of the reference electrode (a compound of $Cr+Cr_2O_3$). This manner of polarization induces lower emf readings, and will therefore predict erroneous lower oxygen contents. It is for this reason that an empirical formulation of the emf versus ppm O relation is used for the CELOX brand emf reading. Finally, a third deficiency is that the oxygen emf probes do not directly detect the presence of solute contents other than oxygen in liquid metals.

In an effort to design probes that can detect dissolved elements other than oxygen, research has been conducted to develop a silicon emf probe for the in situ measuring of silicon (Si) levels in liquid metals (see M. Iwase, H. Abe, and H. Iritani, *Steel Research* 59, No. 10, pp. 433–437 (1988)). In general, stabilized zirconia electrolytes are coated with a metal silicate to define the oxygen chemical potential at the liquid iron-electrolyte interface, e.g., $Mg_2SiO_4$, $ZrSiO_4$, and $Na_2Si_2ZrO_2$. However, because of the lack of thermodynamic data on all the components of the silicon emf probe, a rigorous theoretical interpretation of the measured silicon probe emf has not been possible. Instead, the percentage of silicon in hot metal versus the probe emf relation is derived by an empirical formulation based on plant tests. As an example, the experimental results obtained by Gomyo et al. (see *Iron and Steelmaker*, 1991, 18(7), 71; 1993, 20(3), 87) using Fe—C—Si melts at 1450° C. and an $(Mo+MoO_2)$ reference electrode are in general accord with the results of measurements made in the blast furnace runner at the United States Steel Fairless Works, reported by McDowell and Clauss (see *Ironmaking Conf. Proc.*, 49, 691, (1990)). The plant tests were made using a SILTEMP brand silicon emf probe available commercially from Leeds & Northrup, with a molybdenum $(Mo+MoO_2)$ reference electrode and a $ZrO_2(MgO)$ electrolyte coated with an undisclosed silicate. In these tests, the hot metal temperatures were in the range of 1425° C.±30° C. At 0.1% of silicon in hot metal, the reproducibility is within ±0.04% Si. This increases to ±0.10% Si at 1.0% Si and to about ±0.15% Si at 1.2% Si.

In most cases, molten silicates and aluminosilicates have been used satisfactorily in silicon emf probes since the ionic transport number in these polymeric melts is close to unity and the solute content of liquid metal can be derived from the measured probe emf using the thermodynamic relation between the probe emf and the solute activity in the liquid metal. However, endeavors to develop emf probes that directly detect carbon (C), sulfur (S), nitrogen (N), phosphorous (P), aluminum (Al), silicon (Si), and chromium (Cr) in liquid metals have not succeeded. This is because the carbides, nitrides, and sulfides used as emf probe electrolytes do not have the desired properties for the ionic conduction of C, N, and S. These elements do dissolve in polymeric melts in ionic form ($C^{2-}$, $N^{3-}$, $S^{2-}$) however.

SUMMARY OF THE INVENTION

The present invention helps to solve the problems associated with the emf probes of the prior art. More specifically, the present invention includes emf probes which can detect the concentrations of C, H, O, S, N, P, Al, Si, and Cr in liquid metals. In a first embodiment, each emf probe generally includes a base having a first end and a second end. A reference electrode is positioned between the first and second ends of the base. A glassy electrolyte is positioned adjacent to the reference electrode. This embodiment of the present invention has a number of applications, which include but are not limited to (a) taking measurements in a blast furnace runner, (b) in transfer ladles before and after hot metal refining, (c) in EAF steelmaking, (d) with a sub-lance in oxygen steelmaking, (e) at the converter turndown, (f) in the tap ladle, and (g) at the ladle furnace operation. In a second embodiment, the emf probe has a base having a first end and a second end and a plurality of reference electrodes positioned between the first and second ends of the base. Each reference electrode has a different electrode reference material positioned thereto. A plurality of glassy electrolytes are each positioned adjacent to a corresponding reference electrode. Possible combinations include, but are not limited to, an Si, S, and P emf probe combination for a blast furnace runner and hot metal transfer ladle applications and a C, O, and S emf probe combination for the applications in various stages of steelmaking operations.

These and other advantages of the present invention will be clarified in the Brief Description of the Preferred Embodiments taken together with the attached drawings in which like reference numerals represent like elements throughout.

BRIEF DESCRIPTION OF THE DRAWINGS

FIG. 1 is a cross-sectional view of an electrochemical cell (emf) probe according to one embodiment of the present invention;

FIG. 2 is an end view of the emf probe shown in FIG. 1 with a cap removed; and

FIG. 3 is an end view of an electrochemical cell probe according to a second embodiment of the present invention with a cap removed.

DETAILED DESCRIPTION OF THE PREFERRED EMBODIMENTS

A first embodiment of an emf probe 10 according to the present invention is shown in FIGS. 1 and 2. A second embodiment is shown in FIG. 3.

As shown in detail in FIGS. 1 and 2, and with particular reference to FIG. 1, a first embodiment emf probe 10 generally includes a base 12, a reference electrode 14, and a glassy electrolyte 16. In molten metal applications, the base 12 is preferably a thermally non-conductive refractory material 20 extending about a longitudinal axis L and forming a first end 22, a second end 24, and an outer surface 26, with the second end 24 of the base 12 forming a base cavity 28 and a slit 30. The slit 30 is approximately 5 mm to 10 mm deep from the second end 24 of the base 12, and helps to prevent gaseous bubbles from being trapped in the base cavity 28 when the second end 24 of the base 12 is immersed into a liquid 32, such as a molten bath of metal, allowing the molten metal to fully contact the glassy electrolyte 16. A first conductor 34, preferably made from Mo or other suitable material, extends between the first end 22 of the base 12 and the second end 24 of the base 12, preferably parallel to the longitudinal axis L of the base 12.

The reference electrode 14 and glassy electrolyte 16 are both positioned inside the base cavity 28 formed by the second end 24 of the base 12, preferably 5 mm to 10 mm from the second end 24 of the base 12. The reference electrode 14 is a combination of a conductive substrate 36 (preferably Mo approximately 15 mm in diameter D1, as shown in FIG. 2) having a third surface 38 and a fourth surface 40. An electrode reference material 14 is positioned on the third surface 38 of the conductive substrate 36, approximately 3 mm to 4 mm in thickness T1. The fourth surface 40 of the conductive substrate 36 is left untreated. A second conductor 44, preferably made from Mo or other suitable material, is connected to the fourth surface 40 of the reference electrode 14 and extends to the first end 22 of the base 12. The second conductor 44 is connected to a sensing unit 46.

The electrode reference material 42 is selected based upon the type of solute element being measured. For example, as shown in the following table, the following reference electrodes materials 42 would be appropriate for the corresponding listed solute:

| Solutes | Reference Electrode Materials | m.p. ° C. |
| --- | --- | --- |
| Al in steel | NiAl | 1639 |
| C in steel & hot metal | Graphite | 3800 |
| Cr in steel | Cr | 1903 |
| Si in steel & hot metal | Mo + Mo$_3$Si | 2070 |
| O in steel | Cr + Cr$_2$O$_3$ | 1903/2265 |
| N in steel & hot metal | Ti + TiN | 1660/2950 |
| S in steel & hot metal | Ti + TiS | 1660/1927 |
| P in hot metal only | Th + ThP | 1775/2950 |

In one method of construction, the reference electrode 14 is formed by plasma spraying a powder mixture of the electrode reference materials 42, depending on the material to be tested, onto the third surface 38 of the conductive substrate 36 to a thickness T1 of about 3 mm to 4 mm. The third surface 38 can be flat or have a convex curvature.

The glassy electrolyte 16 has a first surface 48 and second surface 50, with the first surface 48 of the glassy electrolyte 16 positioned adjacent to the slit 30 formed by the second end 24 of the base 12. The second surface 50 of the glassy electrolyte 16 is in direct contact with the electrode reference material 42 positioned adjacent the third surface 38 of the conductive substrate 36. The glassy electrolyte 16 is a pre-fused aluminosilicate of the alkaline-earth elements, such as Mg, Ca, Ba, etc. or a pre-fused sodium silicophosphate. The preferred glassy electrolyte 16 is made from calcium aluminosilicate containing approximately 38% CaO, 42% SiO$_2$, and 20% Al$_2$O$_3$ (eutectic melting point of about 1250° C.). For non-ferrous metals with melting points lower than those of the iron alloys, the glassy electrolyte 16 should have corresponding lower melting points than the calcium aluminosilicate. For example, for the solute measurements in molten copper at temperatures of 1150° C. to 1250° C., suitable glassy electrolytes 16 are soda glass or pyrex powder. In the case of solute measurements in molten aluminum, the glassy electrolyte 16 can be a pre-fused mixture of cryolite (Na$_3$AlF$_6$) admixed with 5% to 10% CaF$_2$ (fluorspar) and 4% to 7% Al$_2$O$_3$ (alumina). This glassy electrolyte 16 has a melting point in the range of 920° C. to 980° C.

The glassy electrolyte 16 is easily made by melting a bulk quantity of a powder mixture of the ingredients, such as CaO, Al$_2$O$_3$, and SiO$_2$. After cooling this homogenized melt, the glassy electrolyte 16 material is crushed into a fine powder and sprayed, such as by plasma spraying, onto the electrode reference material 42, positioned adjacent the conductive substrate 36, to a thickness T2 of about 3 mm to 4 mm.

In certain applications, the cap 18 is positioned on the second end 24 of the base 12. The cap 18 is preferably made from a metal having a low melting point, and helps prevent contamination of the glassy electrolyte 16 as the probe 10 is immersed through material floating on top of the liquid 32 to be tested, such as a slag 52 layer formed over a hot metal bath.

In operation, the emf probe 10 according to the present invention can be used to measure the solute content of a variety of elements in a liquid metal, such as metallic Al, C, Cr, Si, gaseous O$_2$, N$_2$, S$_2$, P$_2$, and other elements, depending on the electrode reference material 42 selected. The emf probe 10 is immersed into a liquid 32, such as a liquid (molten) metal, with the cap 18 preventing slag 52 contamination during emersion. As the emf probe 10 is immersed deeper into the liquid metal, the cap 18 melts, allowing the hot metal to enter the slit 30 formed by the second end 24 of the base 12. Any air present between the liquid metal and the reference electrode 14 can escape through the slit 30 formed in the second end 24 of the base 12. This allows direct contact between the glassy electrolyte 16 and the liquid metal.

The glassy electrolyte 16 melts and is retained in direct contact with the surface of the reference electrode 14 by ferrostatic pressure. This configuration generates an open circuit emf across the first conductor 34 and the second conductor 44 attached to the reference electrode 14. A temperature probe 54 may also be added, such as the U-shaped silica thermocouple shown in FIGS. 1–2. The second embodiment, shown in FIG. 3, also shows a base 12' having a second end 24' approximately 50 mm diameter D2, with three glassy electrolytes 16 positioned adjacent thereto.

To further aid those skilled in the art, the remainder of the Detailed Description describes the mathematical equations and substitution values used to develop the first and second embodiments of the present invention. A general mathematical background applicable to each of the specific types of emf probes is discussed first, and then each specific type of emf probe is discussed in turn. No reference should be made to the figures from this point on unless specifically noted.

Mathematical Background of the Present Invention

For solely ionic conduction in the electrolyte, as in the present invention, the following thermodynamic formulation applies to metallic elements dissolved in liquid metals:

$$E(mV) = \frac{10^{-3}RT}{ZF} \ln \frac{[\alpha_i]_m}{(\alpha_i)_r} \tag{1}$$

where Z is the valency of the solute (i) and subscripts (m) and (r) are for the liquid metal and reference electrode, respectively. Inserting the values of the gas constant R=8.314 J/Mol K, the Faraday constant R=96,489 J/volt equivalent, and changing ln to log, Equation (1) becomes:

$$\frac{5.04 E \times Z}{T} = \log[\alpha_i]_m - \log(\alpha_i)_r \tag{2}$$

The positive and negative signs for (m) and (r) are chosen such that for all solutes, the cell emf increases as the solute content of the liquid metal increases. Moreover, an emf correction has to be made to Equation (2) for the thermal emf at the electrode and liquid metal-Mo conductor junctions.

The solute activity in liquid iron as a function of the solute mass concentration is given by the following thermodynamic equation, with respect to the pure element $$\log[\alpha_i] = \frac{RT \log[\% i] f_i}{\Delta G_s} \tag{3}$$

where $\Delta G_s$ is the free energy of solution of the element (i) in liquid iron for 1 mass (%i), and ($f_1$) being the solute activity coefficient.

Sample numerical values for Equation (3) are derived from the following thermochemical data compiled by Barin et al. and Turkodogan (see I. Barin and O. Knacke, *Thermochemical Properties of Inorganic Substances,* Springer-Verlag, Berlin, 1973, I. Barin, O. Knacke, and O. Kubaschewski, *Thermochemical Properties of Inorganic Substances-Supplement,* Springer-Verlag, Berlin, 1977, and E. T. Turkdogan, *Fundamentals of Steelmaking,* The Institute of Materials, London, 1996). For most of the substances considered, the standard free energies of formation of compounds are accurate within ±(5 to 20) kJ; for ThS and ThP, uncertainty is probably >±40 kJ.

Solubility of Carbon (Graphite) in Liquid Iron

Fe—C melts:

$$\%C = 0.598 + 2.57 \times 10^{-3} T \tag{A1}$$

where T is in degree K.

In hot metal, the only consideration is the effect of silicon on the carbon solubility in iron. This yeilds:

$$\%C = 0.598 + 2.57 \times 10^{-3} T - 0.27[\%Si] \tag{A2}$$

Solute Activities in Liquid Iron

The solute activity in liquid iron with respect to the pure element as a function of the solute mass concentration, is given by:

$$\log[\alpha_i]_m = \frac{RT \log[\% i] f_i}{\Delta G_s} \tag{A3}$$

where $\Delta G_s$ is the free energy of solution of the element (i) in liquid iron for 1 mass %i and $f_i$ is the solute activity coefficient. The thermochemical data given below are for the solutes considered in the remainder of the Detailed Description:

Al(l)=[Al]:

$$\log[\alpha_{Al}]_m = \log[\% Al] f_{Al} - \frac{3300}{T} - 1.46 \tag{A4}$$

C(gr.)=[C]:

$$\log[\alpha_C]_m = \log[\% C] f_C + \frac{1180}{T} - 2.21 \tag{A5}$$

Cr(s)=[Cr]:

$$\log[\alpha_{Cr}]_m = \log[\% Cr] f_{Cr} + \frac{1005}{T} - 2.45 \tag{A6}$$

Si(l)=[Si]:

$$\log[\alpha_{Si}]_m = \log[\% Si] f_{Si} - \frac{6869}{T} - 0.90 \tag{A7}$$

Gas Solubilities in Liquid Iron

Equilibrium constant for gas

| Reaction | partial pressure in atm. | |
|---|---|---|
| $\frac{1}{2} N_2 = [N]$ | $\log \frac{[ppm\ N]}{(p_{N_2})^{1/2}} = -\frac{188}{T} + 2.76 - \log f_N$ | (A8) |
| $\frac{1}{2} O_2 = [O]$ | $\log \frac{[ppm\ O]}{(p_{O_2})^{1/2}} = \frac{6046}{T} + 4.24 - \log f_O$ | (A9) |
| $\frac{1}{2} S_2 = [S]$ | $\log \frac{[\% S]}{(p_{S_2})^{1/2}} = \frac{7055}{T} - 1.22 - \log f_S$ | (A10) |
| $\frac{1}{2} P_2 = [P]$ | $\log \frac{[\% P]}{(p_{P_2})^{1/2}} = \frac{6382}{T} + 1.01 - \log f_P$ | (A11) |

In low alloy steels, the activity coefficients $f_i$ of these solutes are close to one. For carbon and silicon contents of hot metal, due account should be taken of the $f_i$ values.

Data for Reference Electrodes

For the solutes involving gases, the chemical potential of the gas at the reference electrode is that for the reaction equilibrium at the electrode-electrolyte interface.

Oxygen Sensor $$1/3\ Cr_2O_3(s) = 2/3\ Cr(s) + 1/2\ O_2 \tag{A12}$$

$$\log(p_{O_2})_r^{1/2} = -\frac{19330}{T} + 4.31$$

Nitrogen Sensor $$TiN(s) = Ti(s) + 1/2\ N_2 \quad (A13)$$

$$\log(p_{N_2})_r^{1/2} = -\frac{17567}{T} + 4.87$$

Sulfur Sensor $$TiS(s) = Ti(s) + 1/2\ S_2 \quad (A14)$$

$$\log(p_{S_2})^{1/2} = -\frac{17422}{T} + 4.36$$

Phosphorus Sensor $$\log(p_{P_2})^{1/2} = -\frac{21709}{T} + 4.48 \quad (A15)$$

$$ThP(s) = Th(s) + 1/2\ P_2$$

For gaseous elements dissolved in liquid iron, Equation (2) is transformed to:

$$\frac{5.04\ ExZ}{T} = \log(p_i)_m^{1/2} - \log(p_i)_r^{1/2} \quad (4)$$

where $(p_i)_m$ is the equilibrium solute gas partial pressure in the liquid metal and $(p_i)_r$ is for the reference electrode.

Using the above thermodynamic equations and the thermochemical data, the following theoretical equations are formulated for the relations between the emf probe readings and the solute contents of liquid steel and hot metal:

1. The Aluminum Sensing emf Probe

The only known suitable solid reference electrode for Al is the intermetallic compound NiAl, which has a congruent melting point of 1639° C. The activity of aluminum, with respect to pure liquid Al is estimated to be $f_{Al} \cong 0.07$ at liquid steel temperatures. At low Al contents in the deoxidized steels, the activity coefficient $f_{Al} \cong 1.0$. From these values, Z=3, and Equations (2) and (A4), the following equation is obtained:

$$\log[\%\ Al] = 0.31 + \frac{3300 + 15.12\ E}{T} \quad (5)$$

Equation 5 holds for any composition of a deoxidation product. For example:

Table 1: Aluminum Examples

TABLE 1

Aluminum Examples

| | E, mV | |
|---|---|---|
| Mass % Al | 1500° C. | 1700° C. |
| 0.01 | −489 | −520 |
| 0.10 | −372 | −389 |

2. The Carbon Sensing emf Probe

With pure graphite as the reference electrode, the following relation is obtained from Equations (2) and (A5) with Z=4:

$$\log[\%\ C]f_C = 2.21 - \frac{1180 + 20.16\ E}{T} \quad (6)$$

in low alloy steels with C<1%, log $f_C$=0.18[%C]. In the hot metal, both C and Si affect the activity coefficient as given by the relation:

$$\log f_C = 0.14[\%C] + 0.08[\%Si] \quad (7)$$

For example:

TABLE 2a

Carbon in Low Alloy Steels

| | E, mV | |
|---|---|---|
| Mass % C | 1500° C. | 1700° C. |
| 0.01 | −312 | −353 |
| 0.5 | −170 | −196 |
| 1.0 | −152 | −175 |

TABLE 2b

Hot Metal at 1400° C. with 0 and 2% Si

| | E, mV | |
|---|---|---|
| Mass % C | 0% Si | 2% Si |
| 3 | −50 | −37 |
| 4 | −28 | −15 |
| 5 | −9 | −7 |

3. The Chromium Sensing emf Probe

In chromium steels of practical interest, the activity coefficient $f_{Cr}$ is close to one. With pure Cr as the reference state, Equations (2) and (A6), and Z=3, the following relation is obtained:

$$\log[\%\ Cr] = 2.45 - \frac{1005 - 15.12\ E}{T} \quad (8)$$

Examples include:

TABLE 3

Chromium Examples

| | E, mV | |
|---|---|---|
| Mass % Si | 1500° C. | 1700° C. |
| 1 | −221 | −253 |
| 10 | −104 | −122 |
| 30 | −47 | −60 |

4. The Silicon Sensing emf Probe

The only suitable solid reference electrode for the silicon probe is the mixture (Mo+Mo$_3$Si). The estimated free energy data give for the silicon activity the following approximate value, with respect to pure liquid silicon.

$$\log(\alpha_{Si})_r = -\frac{6458}{T} + 1.54 \quad (9)$$

From Equations (2), (9), and (A7), with Z=4, the following equation is obtained:

$$\log[\%\text{Si}]f_{Si} = 2.44 + \frac{411 + 20.16\,E}{T} \quad (10)$$

where log $f_{Si}$=0.92 for the average hot metal composition range 4 to 5%C and Si<1%.
For example:

TABLE 4

Silicon Examples

| Mass % Si | E, mV | |
|---|---|---|
| | 1300° C. | 1500° C. |
| 0.1 | −217 | −242 |
| 0.5 | −142 | −180 |
| 1.0 | −119 | −154 |

5. The Oxygen Sensing emf Probe

The temperature dependence of $(p_{O_2})_r^{1/2}$ for the reference electrode $Cr+Cr_2O_3$ is given by $$\log(p_{O_2})_r^{1/2} = -\frac{19330}{T} + 4.31 \quad (11)$$

Inserting Equations (11) and (A9) into Equation (2), with Z=2, gives for the oxygen activity in liquid iron:

$$\log[\alpha_O] = \log[ppm\,O]f_O = 8.55 - \frac{13284 - 10.08\,E}{T} \quad (12)$$

The effects of alloying elements and deoxidants on the activity coefficient $f_O$ is given by the following summation:

$$\log f_O = -3.90[\%\text{Al}] - 0.13[\%\text{C}] - 0.04[\%\text{Cr}] - 0.13[\%\text{Si}] \quad (13)$$

For example:

TABLE 5

Oxygen Examples

| [ppm O]$f_O$ | E, mV | |
|---|---|---|
| | 1500° C. | 1700° C. |
| 1 | −186 | −356 |
| 10 | −10 | −160 |
| 100 | 166 | 36 |
| 1000 | 341 | 232 |

There should be no perceptible electrode polarization at high oxygen contents in steel with only a 3 mm to 4 mm thick molten electrolyte, hence, Equation (12) is applicable.

6. The Nitrogen Sensing emf Probe

From Equations (2), (A8), and (A13), with Z=3, the theoretical relation for the nitrogen emf probe is:

$$\log[ppm\,N]f_N = 7.63 - \frac{17755 - 15.12\,E}{T} \quad (16)$$

In low alloy steels, $f_N$ is close to one. In hot metal, only carbon and silicon have major effects on $f_N$ as given below:

$$\log f_N = 0.13[\%\text{C}] + 0.047[\%\text{Si}] \quad (17)$$

For an average melt temperature of 1400° C. and 0.6% Si in the hot metal, the average carbon content is 4.74% C, for which $f_N$=4.41. For example:

TABLE 6a

Nitrogen Examples for Low Alloy Steels

| ppm N | E, mV | |
|---|---|---|
| | 1500° C. | 1700° C. |
| 10 | 397 | 309 |
| 100 | 514 | 440 |

TABLE 6b

Nitrogen Examples for Hot Metal with an Average of 4.74% C and 0.6% Si

| ppm N | E, mV | |
|---|---|---|
| | 1300° C. | 1500° C. |
| 10 | 552 | 472 |
| 100 | 656 | 590 |

7. The Sulfur Sensing emf Probe

Inserting Equations (A10) and (A14) into (2), with Z=2, yields:

$$\log[\%\text{S}]f_S = 3.13 - \frac{10367 - 10.08\,E}{T} \quad (18)$$

In low alloy steels, $f_S$ is about one. For the hot metal composition range 4% to 5% C, Si<2%, Mn<2%, the log $f_S$ summation is:

$$\log f_S = 0.147[\%\text{C}] + 0.063[\%\text{Si}] - 0.026[\%\text{Mn}] \quad (19)$$

which gives for the average values of 4.74% C, 0.6% Si, and 1% Mn, $f_S$=5.11. Examples include:

TABLE 7a

Sulfur Examples for Low Alloy Steels

| Mass % S | E, mV | |
|---|---|---|
| | 1500° C. | 1700° C. |
| 0.001 | −50 | −171 |
| 0.01 | 126 | 24 |
| 0.10 | 302 | 220 |

TABLE 7b

Sulfur Examples for Hot Metal With an Average of 4.74% C, 0.6% Si, and 1% Mn

| Mass % S | E, mV | |
|---|---|---|
| | 1300° C. | 1500° C. |
| 0.001 | 183 | 75 |
| 0.01 | 339 | 251 |
| 0.10 | 495 | 427 |

8. The Phosphorus Sensing emf Probe

The proposed phosphorus emf probe with a Th+ThP compound reference electrode can be used only under reducing conditions, i.e., $p_{O_2} < ^{-18}$ atm, so that the phosphorus ions in the molten probe electrolyte remain in the trivalent state as phosphide ions $P^{3-}$. Therefore, the practical application of this phosphorus emf probe may be limited to carbon-saturated hot metal, although other applications are clearly contemplated. It is for these conditions that the following theoretical relation is derived from Equations (2), (A11), and (A15), with Z=3:

$$\log[P]f_P = 5.49 - \frac{15327 - 15.12\,E}{T} \quad (20)$$

The activity coefficient $f_P$=2.0 for the average contents of 4.74% C and 0.6% Si in the hot metal.

TABLE 8

Phosphorus Examples for Hot Metal Containing 4.74% C and 0.6% Si

| Mass % P | E, mV | |
|---|---|---|
| | 1300° C. | 1500° C. |
| 0.01 | 224 | 171 |
| 0.10 | 370 | 288 |

For emf probe measurements of phosphorus in liquid metal refining processes under oxidizing conditions, as, for example, in steelmaking and refining of blister copper, the glassy electrolyte to be used is pre-fused sodium silicophosphate containing 30% $Na_2O$+60% $SiO_2$+10% $P_2O_5$. This powdered glass will be plasma sprayed on the reference electrode disc, which is a 1:1 mixture of Ta+$Ta_2O_5$. The following are the estimated sensor emf readings at 1600° C. in low allow steels:

| % P | mV |
|---|---|
| 0.005 | −620 |
| 0.05 | −496 |

9. The Hydrogen Sensing emf Probe

The metal hydrides are not stable at elevated temperatures and ambient pressures. However, there is sufficient solid solubility of hydrogen in titanium such that it could be used as the reference electrode. From experimental data gathered by McQuillan (see A. D. McQuillan, *Proc. Royal Soc.*, London, 1950, Ser. A204, 309) on the solid solubility of hydrogen in β-Ti, the following equilibrium value of $p_{H_2}$ (atm) is obtained for β-Ti containing 0.1 wt. % H:

$$\log(p_{H_2})_r^{1/2} = -\frac{3040}{T} + 1.52 \quad (21)$$

For this reference electrode, $p_{H_2}$=0.04 atm at 1100° C. increasing to 0.62 atm at 1600° C. The hydrogen solubility in liquid iron alloys is given by the following equilibrium relation:

$$\log \frac{[ppm\,H]}{(p_{H_2})^{1/2}} = -\frac{1900}{T} + 2.423 - \log f_H \quad (22)$$

Inserting Equations (21) and (22) into (2) with Z=1 gives the following theoretical relation:

$$\log[ppm\,H]f_H = -\frac{4940 - 5.04\,E}{T} + 3.943 \quad (23)$$

TABLE 9a

Hydrogen Examples for Liquid Steel

| [ppm H]$f_H$ | E, mV | |
|---|---|---|
| | 1400° C. | 1600° C. |
| 1 | −329 | −485 |
| 10 | 3 | −114 |

The equilibrium relation for hydrogen solubility in liquid copper is given by:

$$\log \frac{[ppm\,H]}{(p_{H_2})^{1/2}} = -\frac{2273}{T} + 2.36 \quad (24)$$

Combining Equations (2), (21), and (24) gives $$\log[ppm\,H]f_H = -\frac{5313 - 5.04\,E}{T} + 3.88 \quad (25)$$

TABLE 9b

Hydrogen Examples for Liquid Copper

| [ppm H]$f_H$ | E, mV | |
|---|---|---|
| | 1100° C. | 1300° C. |
| 1 | −3 | −157 |
| 10 | 270 | 155 |

As illustrated in the preceding Detailed Description, the first and second embodiments of the present invention can be used to measure solute concentrations of C, H, O, S, N, P, Al, Si, and Cr in liquid metals. The first embodiment is generally directed to a single emf probe, wherein the second embodiment shows two or more emf probes incorporated into a single base.

The invention has been described with reference to the preferred embodiments. Obvious modifications and alterations will occur to others upon reading and understanding the preceding Detailed Description. It is intended that the invention be construed as including all such modifications and alterations insofar as they come within the scope of the appended claims or the equivalents thereof.

I claim:

1. An electrochemical cell probe for measuring concentrations of elements in a liquid comprising:

a base having a first end and a second end;

a reference electrode positioned between the first end of the base and the second end of the base; and a glassy electrolyte positioned adjacent the reference electrode, wherein when the base is inserted into the liquid, the base and the glassy electrode are in direct contact with the liquid, wherein the glassy electrolyte is selected from the group consisting essentially of a compound of 38% CaO, 42% $SiO_2$, and 20% $Al_2O_3$, soda glass, Pyrex powder, a compound of 30% $Na_2O$, 60% $SiO_2$, and 10% $P_2O_5$ and a pre-fused mixture of cryolite ($Na_3AlF_6$) admixed with approximately 5% to 10% $CaF_2$ (fluorspar) and approximately 4% to 7% $Al_2O_3$.

2. The electrochemical cell probe as claimed in claim 1 wherein the base is a non-conducting refractory material.

3. The electrochemical cell probe as claimed in claim 1 wherein the second end of the base forms a base cavity and a slot.

4. The electrochemical cell probe as claimed in claim 1 further comprising a first conductor extending between the first end of the base and the second end of the base.

5. The electrochemical cell probe as claimed in claim 1 wherein the reference electrode is formed by a substrate coated with a electrode reference material selected from the group consisting of NiAl, graphite, Cr, a compound of Mo and $Mo_3Si$, a compound of Cr and $Cr_2O_3$, a compound of Ti and TiN, a compound of Ti and TiS, a compound of Ta and $Ta_2O_5$, and a compound of Th and ThP.

6. The electrochemical cell probe as claimed in claim 5 wherein the substrate is formed from Mo.

7. The electrochemical cell probe as claimed in claim 1 wherein the glassy electrolyte is positioned inside the base cavity approximately 5 mm to 10 mm from the first end of the base.

8. The electrochemical cell probe as claimed in claim 1 wherein the glassy electrolyte is selected from the group consisting essentially of a pre-fused aluminosilicate of the alkaline-earth elements and a pre-fused sodium silicophosphate.

9. The electrochemical cell probe as claimed in claim 1 further comprising a cap positioned adjacent the second end of the base.

10. The electrochemical cell probe as claimed in claim 1 further comprising a temperature probe extending from the first end of the base to the second end of the base.

11. The electrochemical cell probe as claimed in claim 10 wherein the temperature probe is a thermocouple.

12. An electrochemical cell probe for measuring elemental concentrations in a molten metal comprising:
- a base having a first end and a second end;
- a plurality of conductive substrates positioned between the first and second ends of the base, each conductive substrate having a different electrode reference material positioned adjacent thereto; and
- a plurality of glassy electrolytes, each positioned adjacent a corresponding reference electrode.

13. The electrochemical cell probe as claimed in claim 12 wherein the electrode reference material selected from the group consisting of NiAl, graphite, Cr, a compound of Mo and $Mo_3Si$, a compound of Cr and $Cr_2O_3$, a compound of Ti and TiN, a compound of Ti and TiS, a compound of Ta and $Ta_2O_5$, and a compound of Th and ThP.

14. An electrochemical cell probe for measuring elemental concentrations in a molten metal comprising:
- a base having a first end, a second end, an external surface, and extending about a longitudinal axis, wherein the second end of the base forms a base cavity and a slit extending across a length of the base cavity, perpendicular to the longitudinal axis of the base;
- a conductive substrate positioned within the base cavity;
- a conductive substrate extending from the first end of the base to the second end of the base;
- a glassy electrolyte consisting essentially of 38% CaO, 42% $SiO_2$, and 20% $Al_2O_3$ in contact with the conductive substrate;
- a second conductor extending from the second end of the base to a first side of the reference electrode;
- a temperature lead extending from the first end of the base to the second end of the base; and
- a sensing unit connected to the first conductor, the second conductor, and the temperature lead.

15. The electrochemical cell probe as claimed in claim 14 further comprising a cap positioned adjacent the second end of the base.

16. The electrochemical cell probe as claimed in claim 14 wherein the reference electrode material is selected from the group comprising NiAl, graphite, Cr, a compound of Mo and $Mo_3Si$, a compound of Cr and $Cr_2O_3$, a compound of Ti and TiN, a compound of Ti and TiS, a compound of Ta and $Ta_2O_5$ and a compound of Th and ThP.

17. The electrochemical cell probe as claimed in claim 14 wherein the glassy electrolyte is cylindrical in shape, is approximately 15 mm diameter, and is approximately 3 mm to 4 mm in thickness.

18. The electrochemical cell probe as claimed in claim 14 wherein the temperature electrochemical field probe is enclosed in a sheath.

* * * * *

UNITED STATES PATENT AND TRADEMARK OFFICE
CERTIFICATE OF CORRECTION

PATENT NO.    : 6,328,867 B1
DATED         : December 11, 2001
INVENTOR(S)   : Ethem Tugrul Turkdogan It is certified that error appears in the above-identified patent and that said Letters Patent is hereby corrected as shown below:

Column 8,
Line 1, "1180 + 20.16 E" should read -- 1180 - 20.16 E --.

Column 12,
Line 59, "the base and the glassy electrode are" should read -- the glassy electrolyte is --.

Column 13,
Line 11, "with a electrode" should read -- with an electrode --.
Line 39, "the first and second ends" should read -- the first end and the second end --.
Line 42, between "electrolytes" and "each" delete comma (,).
Line 43, after "corresponding" delete "reference electrode" and insert -- one of the different electrode reference material, wherein the glassy electrolytes each is selected from the group consisting essentially of a compound of 38% CaO, 42% $SiO_2$, and 20% $Al_2O_3$, soda glass, Pyrex powder, a compound of 30% $Na_2O$, 60% $SiO_2$, and 10% $P_2O_5$ and a pre-fused mixture of cryolite ($Na_3AlF_6$) admixed with approximately 5% to 10% $CaF_2$ (fluorspar) and approximately 4% to 7% $Al_2O_3$. --.

Column 14,
Line 2, "wherein the electrode" should read -- wherein the different electrode --.
Line 2, "material selected" should read -- material is selected --.
Line 14, "a conductive substrate positioned" should read -- a reference electrode positioned --.
Line 15, "a conductive substrate extending" should read -- a first conduct extending --.
Lines 18-19, "with the conductive substrate;" should read -- with the reference electrode; --.

Signed and Sealed this

Tenth Day of September, 2002

*Attest:*

JAMES E. ROGAN
*Attesting Officer*   *Director of the United States Patent and Trademark Office*